(12) United States Patent
Eichler (10) Patent No.: US 8,894,605 B2
(45) Date of Patent: Nov. 25, 2014

(54) OPHTHALMOSURGICAL SYSTEM

(75) Inventor: Michael Eichler, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 447 days.

(21) Appl. No.: 12/872,592

(22) Filed: Aug. 31, 2010

(65) Prior Publication Data

US 2011/0054385 A1 Mar. 3, 2011

Related U.S. Application Data

(63) Continuation of application No. PCT/EP2009/001747, filed on Mar. 11, 2009.

(30) Foreign Application Priority Data

Mar. 12, 2008 (DE) .................... 10 2008 013 950

(51) Int. Cl.
*A61M 1/00* (2006.01)
*A61F 9/007* (2006.01)
*A61M 3/02* (2006.01)

(52) U.S. Cl.
CPC .......... *A61M 1/0058* (2013.01); *A61F 9/00745* (2013.01); *A61M 3/0241* (2013.01); *A61M 3/0258* (2013.01); *A61M 2210/0612* (2013.01)
USPC .................. 604/30; 604/27; 604/35; 604/118

(58) Field of Classification Search
USPC ........... 604/22, 27, 30, 35, 118, 119, 121, 43, 604/73
See application file for complete search history.

(56) References Cited

U.S. PATENT DOCUMENTS 4,054,137 A * 10/1977 Lee et al. .................... 604/38
4,369,785 A 1/1983 Rehkopf
(Continued)

FOREIGN PATENT DOCUMENTS

EP 0 717 970 6/1996

OTHER PUBLICATIONS

English translation of the German Office Action for corresponding DE Appl No. 10 2008 013 950.5, dated Nov. 14, 2008.
(Continued)

*Primary Examiner* — Kevin C Sirmons
*Assistant Examiner* — Shefali Patel
(74) *Attorney, Agent, or Firm* — Fish & Richardson P.C.

(57) ABSTRACT

The disclosure relates to an ophthalmosurgical system that includes a first irrigation fluid source. The system also includes a first irrigation fluid line connected to the first irrigation fluid source at a first end and open at a second end. The system further includes an aspiration fluid line, by which a fluid can be removed from an ocular lens. In addition, the system includes a suction pump, to which the aspiration fluid line is connected, and a second irrigation fluid source, to which a second irrigation fluid line is connected. The second irrigation fluid line is connected to the first irrigation fluid line at a coupling site. The system also includes a first valve, which is disposed between the first end of the first irrigation fluid line and the coupling site, and a second valve, which is disposed between the second irrigation fluid source and the coupling site.

21 Claims, 6 Drawing Sheets

(56) References Cited

U.S. PATENT DOCUMENTS

| | | | |
|---|---|---|---|
| 5,342,293 A | 8/1994 | Zanger | |
| 5,649,905 A | 7/1997 | Zanger | |
| 5,676,650 A | 10/1997 | Grieshaber et al. | |
| 5,697,898 A * | 12/1997 | Devine | 604/22 |
| 5,700,240 A * | 12/1997 | Barwick et al. | 604/22 |
| 2009/0163853 A1 * | 6/2009 | Cull et al. | 604/35 |

OTHER PUBLICATIONS

English translation of the Chinese Office for corresponding CN Appl No. 2009-80108435.5, Action dated Dec. 15, 2011.

International Search Report issued on Jul. 6, 2009, for the corresponding PCT application No. PCT/EP2009/001747, filed Mar. 11, 2009.

* cited by examiner

OPHTHALMOSURGICAL SYSTEM

CROSS-REFERENCE TO RELATED APPLICATIONS

This application is a continuation of, and claims benefit under 35 USC §120 to, international application PCT/EP/2009/001747, filed Mar. 11, 2009, which claims the benefit of German Application No. 10 2008 013 950.5, filed Mar. 12, 2008. International application PCT/EP2009/001747 is hereby incorporated by reference in its entirety.

FIELD

The disclosure relates to an ophthalmosurgical system, such as for carrying out phacoemulsification.

BACKGROUND

There are a number of surgical techniques for treating clouding of the lens, referred to as a cataract or being pearl-eyed. The most common technique is phacoemulsification, in which a thin tube in the form of a hollow needle is inserted into the ocular lens and excited to oscillate via ultrasound. The vibrating needle emulsifies the lens in the direct vicinity thereof such that the lens fragments generated can be suctioned away through a line via a pump. Once the lens has been completely emulsified, a new artificial lens can be inserted into the empty lens capsule and so a patient treated in this fashion again obtains good vision.

In phacoemulsification, use is made of a device that in general has a source with irrigation fluid, an irrigation fluid line for supplying irrigation fluid to the ocular lens to be treated, a needle that can oscillate and is in a handpiece, and a suction line (aspiration line) for removing emulsified lens fragments into a collection container.

The irrigation fluid source is arranged higher up than the ocular lens to be treated, and so the irrigation fluid or rinsing fluid can flow to the eye with hydrostatic pressure. Depending on application, the irrigation fluid source can usually be displaced to different heights, and so a different hydrostatic pressure can be obtained. For this purpose, the irrigation fluid source is hung onto a rod that can be driven by a motor and thus attains various heights. Such displacement of the irrigation fluid source involves a few seconds for the desired height to be reached. Furthermore, it can be necessary to wait for pressure variations induced by the displacement of the irrigation fluid source to have died down before an operation can be continued. The height of the displacement of such a source has mechanical limits due to the rod. Hence, the maximum hydrostatic pressure of the irrigation fluid is prescribed by the achievable height of the irrigation fluid source.

In practice it was found that different operations on the eye can involve different fluid pressures. An operation on the front section of the eye can involve a different pressure than an operation on the back section of the eye. Moreover, different operations in each case can involve different instruments, such as needles with differing diameters for a phacoemulsification handpiece, wherein work is undertaken with different pressures. The fluid pressures that can be achieved in currently available systems for phacoemulsification often do not suffice for such applications.

Additionally, there is a trend in minimally invasive surgery for an incision to be carried out with ever smaller instruments or needles. The reason for this trend mainly lies in the fact that post-operative treatment of a patient has to be carried out less often as the size of the cut carried out in the operation decreases. In the case of a very small cut, there may be no need for aftercare, and so no further complications may occur. The use of hollow needles with very small diameters, e.g. greater than 23 gauge, however can mean a high tube friction coefficient for the flowing fluid. For comparison, reference is made to the fact that an external diameter of 25 gauge corresponds to an outer diameter of 0.5 mm. However, as the diameter of the needle decreases, the pressure with which the fluid is transported through the pipe line or needle generally increases in order to achieve the same fluid volume flow. In the known ophthalmosurgical systems, the available fluid pressure often does not suffice for this.

Additionally, a higher irrigation fluid pressure may be desired very quickly during an operation. Displacing the irrigation fluid source then may involve too much time and/or may not provide the desired pressure, and so complications during the operation may occur.

SUMMARY

The disclosure provides a surgical system for treating eye disorders via the phacoemulsification technique without involving post-operative treatment, using relatively small hollow needles while also providing a high and stable fluid pressure in a very short time.

An ophthalmosurgical system includes a first irrigation fluid source, and a first irrigation fluid line, which is connected to the first irrigation fluid source at a first end and is open at the other end such that fluid can be transported from the irrigation fluid source to the open end and from there to an ocular lens to be treated. The system also includes an aspiration line by which fluid can be removed from the ocular lens, and a suction pump, to which the aspiration fluid line is connected. The system further includes a second irrigation fluid source, to which a second irrigation fluid line is connected. The second irrigation fluid line is connected to the first irrigation fluid line at a coupling site, so that irrigation fluid can be supplied into the first irrigation fluid line from the second irrigation fluid line. A fluid pressure from the first irrigation fluid source can be built up using the second irrigation fluid source. The fluid pressure is higher than can be achieved at most in the case of the first irrigation fluid source. In addition, the system includes a first valve arranged between the first end of the first irrigation fluid line and the coupling site, and a second valve arranged between the second irrigation fluid source and the coupling site.

Two irrigation fluid sources are provided in this system, wherein the second irrigation fluid source can provide a higher fluid pressure than the first irrigation fluid source. The valves can each be controlled such that in each case only one irrigation fluid source or both irrigation fluid sources supply fluid into the first irrigation fluid line. If there is no need for high fluid pressure, work can be undertaken using the first irrigation fluid source. In the case of high fluid pressure it is possible to add in the second irrigation fluid source or the latter can be used as an alternative to the first irrigation fluid source. By way of example, the second irrigation fluid source can have pressurized fluid or be arranged sufficiently high in the room, for example directly under the ceiling, such that there is high hydrostatic pressure. If high fluid pressure is involved during an operation, the first valve is connected such that the fluid from the second irrigation fluid source flows exclusively in the direction of the ocular lens to be treated and not in the direction toward the first irrigation fluid source. The valves also allow simple implementation of a quick switch between conventional pressure and high pressure. It may no longer necessary to displace an irrigation fluid container to a certain height via a rod and wait until pressure variations in the system have died down to an acceptable level. Operations in which normal and high fluid pressures are envisaged can therefore be carried out with increased safety. Thus, such a system allows the use of relatively large, but also very small, operation needles in a handpiece during phacoemulsification.

In some embodiments, the suction pump is a first piston pump, which is provided with a controllable drive, wherein the piston pump is suitable for holding aspirated fluid in the piston cylinder thereof. In contrast to the conventional peristaltic pump, a piston pump allows a constant volume flow at constant fluid pressure during a stroke, and so aspiration can be carried out with high eye stability. Pressure variations or irregular and impulsive or jerky supply of fluid, as can be present, in principle, in peristaltic pumps do not occur during the use of a piston pump, where the motion is not cyclical and at a high frequency but only with one stroke along the piston cylinder. In order to keep abrasion of the piston or the sealant between piston and cylinder wall as low as possible, the piston pump can be exchanged after one or only a few strokes. Furthermore, the piston pump allows very precise dosing in the case of small delivered quantities, and so reliable aspiration can also be achieved when very small needles with only a very small volume flow are used.

A third valve can be arranged in the aspiration line between the ocular lens to be treated and the first piston pump. Such a valve can reliably prevent aspirated fluid flowing back in the direction of the ocular lens in the case of pressure variations.

The second irrigation fluid source can be a second piston pump, which is provided with a controllable drive, wherein the second piston pump is suitable for dispensing irrigation fluid contained in the piston into the second irrigation fluid line. The aforementioned advantages of the piston pump equally hold true if the piston pump is used for the irrigation. A constant volume flow at constant pressure in a closed system, which volume flow is additionally free from pressure variations, can thus be implemented in a very simple fashion. Additionally, the second piston pump affords the possibility of supplying the irrigation fluid into the first irrigation fluid line at a very high pressure.

In some embodiments, a fourth valve can be provided in the first irrigation fluid line, where the fourth valve is arranged between the coupling site with the second irrigation fluid line and the open end of the first irrigation fluid line. This valve can be connected such that no more fluid flows between the coupling site and the open end of the first irrigation fluid line, so that irrigation fluid from the first irrigation fluid source can be supplied into the container of the second irrigation fluid source via the first valve. When the second piston pump is used, the piston can thus suction the fluid into the piston cylinder during a backward motion, and so the irrigation fluid can be squeezed out during a forward motion of the piston.

In some embodiments, the ophthalmosurgical system according to the disclosure has a third irrigation fluid source, which is connected to the aspiration line via a third irrigation fluid line, wherein a fifth valve is provided in the third irrigation fluid line. If an occlusion occurs in the aspiration fluid line such that negative pressure is formed in the aspiration fluid line if the suction pump is switched on, a relatively large amount of fluid can be suctioned out of the eye at the moment when this occlusion is pierced. So as not to endanger the eye chamber stability, fluid can be supplied into the aspiration line by the third irrigation fluid source in such a case. The third irrigation fluid source can be a third piston pump, which is provided with a controllable drive, wherein the third piston pump is suitable for dispensing irrigation fluid contained in the piston into the aspiration line. A large fluid volume at high pressure can quickly be provided by appropriate actuation of the third piston pump.

In some embodiments, the third irrigation fluid source is connected to the first irrigation fluid source via a filling line, in which a sixth valve is arranged. Hence, pressure balance in the aspiration line can be realized with an appropriately connected sixth valve such that there is complete separation from the first irrigation fluid source. Therefore, no pressure variations are excited in the first irrigation fluid line when an occlusion is pierced or when the aspiration fluid line is ventilated, and so high eye chamber stability can be achieved.

BRIEF DESCRIPTION OF DRAWINGS

Further advantages and features of the disclosure are explained with reference to the figures illustrated below, in which.

DETAILED DESCRIPTION

Figure 1:
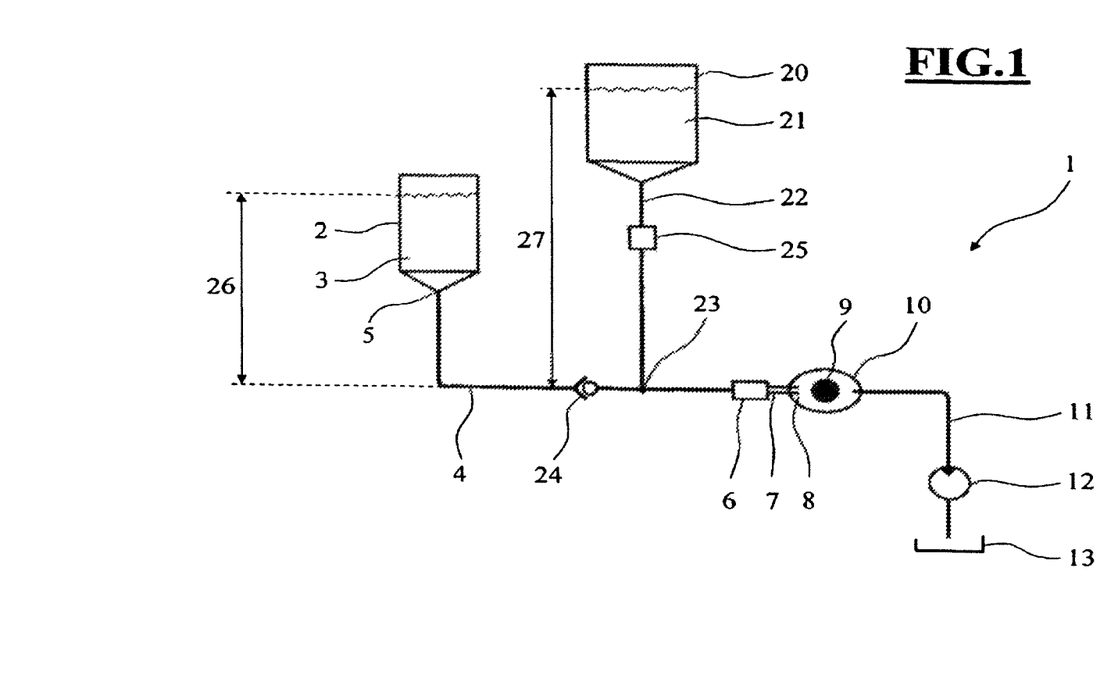
FIG. 1 shows a schematic illustration of a first embodiment of the ophthalmosurgical system according to the disclosure.

FIG. 1 shows a schematic illustration of a first embodiment of the ophthalmosurgical system 1 according to the disclosure. A first irrigation fluid source 2 contains irrigation fluid 3, which can flow from a first end 5 through a first irrigation fluid line 4 in the direction toward a handpiece 6 with a needle 7 and an end 8 that is open there. During phacoemulsification, the needle 7 is inserted into the ocular lens 9 to be treated of the eye 10, wherein the needle oscillates with ultrasound and the lens is emulsified into small particles. The irrigation fluid source 2 is arranged at a greater height than the ocular lens 9, and so the irrigation fluid 3 can flow in the direction of the ocular lens 9 with a hydrostatic pressure 26. In phacoemulsification, the emulsified particles are transported away together with the supplied fluid through an aspiration line 11, to which a suction pump 12 is connected, which can deposit the suctioned-off fluid including emulsified particles in a collection container 13.

In the system 1 illustrated in FIG. 1, provision is made for a second irrigation fluid source 20 with irrigation fluid 21 and a second irrigation fluid line 22 such that the second irrigation fluid line 22 is coupled to the first irrigation fluid line 4 at a coupling site 23. Hence, the irrigation fluid 21 can flow through the irrigation fluid line 22 to the coupling site 23 and from there in the direction toward the handpiece 6 or needle 7 via the first irrigation fluid line 4. Arranged between the first end 5 of the first irrigation fluid line 4 and the coupling site 23 there is a first valve 24, which is used to interrupt or release the volume flow between the first irrigation fluid source 2 and the coupling site 23. The first valve can be a passive valve or an actively controlled valve. A second valve 25 is arranged between the second irrigation fluid source 20 and the coupling site 23. This second valve 25 can be actuated such that irrigation fluid 21 can flow through the second irrigation fluid line 22 in the direction toward the handpiece 6 and there in the direction toward the ocular lens 9 to be treated via the coupling site 23. In such a case, in which the irrigation fluid 21 flows at high pressure in the second irrigation fluid line 22 and between the coupling site 23 and the handpiece 6, the first valve 24 is desirably closed in order to ensure that the fluid 21 does not flow to the first irrigation fluid source 2. The relatively high fluid pressure provided by the second irrigation fluid source 20 can be achieved, for example, by virtue of the fact that the second irrigation fluid source 20 is arranged higher than the first irrigation fluid source 2, and so there is a higher hydrostatic pressure 27 compared to the hydrostatic pressure 26. However, the irrigation fluid 21 can for example also be present under relatively high container pressure within the second irrigation fluid source such that a higher fluid pressure compared to the first irrigation fluid source 2 can be achieved even in the case of equal height.

Figure 2:
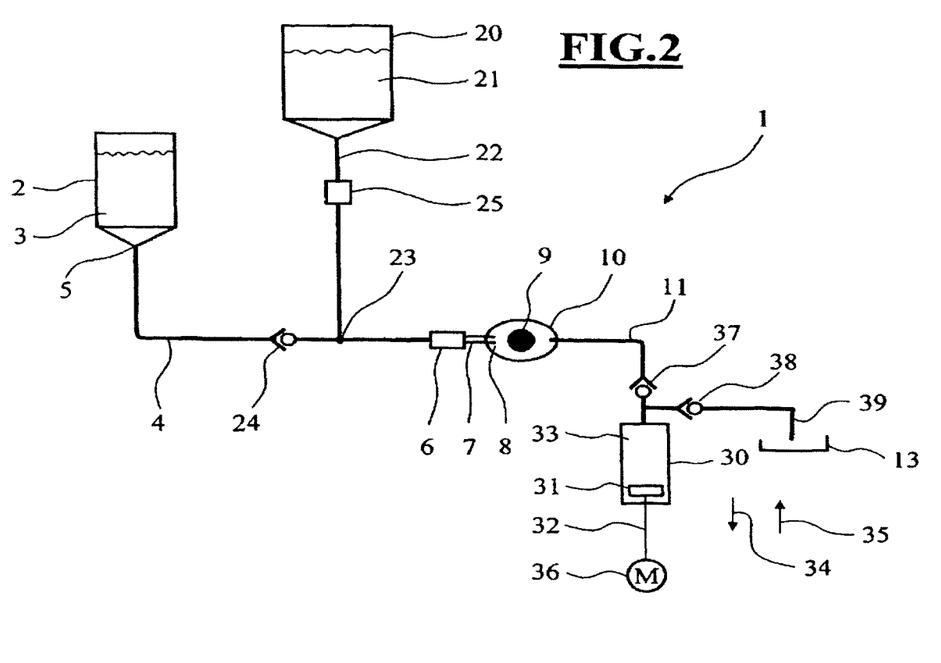
FIG. 2 shows a schematic illustration of a second embodiment of the ophthalmosurgical system according to the disclosure.

FIG. 2 shows that in one embodiment of the disclosure the suction pump connected to the aspiration line 11 can be designed as a piston pump 30, which has a piston 31 with a piston rod 32 that can both be displaced in a piston cylinder 33. If the piston 31 is moved back via a drive 36 via the piston rod 32 (see arrow 34) the piston cylinder 33 takes up aspirated fluid and particles. Pressure variations, which are common in a peristaltic pump, can be reliably avoided with the use of such a piston pump if the piston 31 only once carries out the backward motion (see arrow 34) during an operation. The piston 31 may not carry out a forward motion (see arrow 35) because otherwise aspirated fluid would be transported back into the eye. In order to reliably avoid this, the fluid flow toward the eye can be interrupted by a valve 37. Once the piston 33 has been filled with fluid and particles, it can, for example, be completely replaced by a piston pump that has not yet been filled. Another option consists of driving the piston 32 after closing the valve 37 such that, in a forward motion (see arrow 35), it transports the fluid out of the piston 33 and into a discharge line 39 with a valve 38 and from there to a collection container 13. Subsequently, the piston 33 can again take up aspirated fluid in a backward motion.

Figure 3:
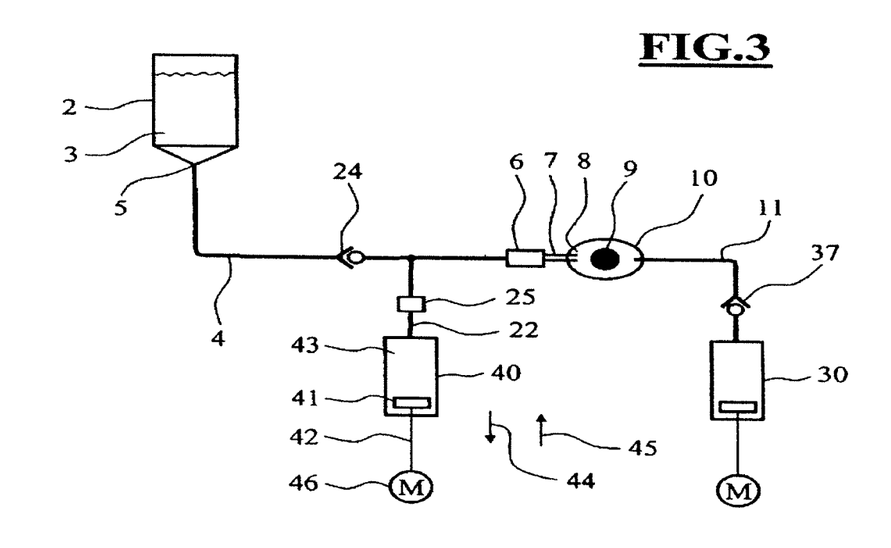
FIG. 3 shows a schematic illustration of a third embodiment of the ophthalmosurgical system according to the disclosure.

FIG. 3 schematically illustrates a third embodiment of the disclosure. Herein, the second irrigation fluid source is a second piston pump 40, with a piston 41 and a piston rod 42, which can both be displaced in a piston cylinder 43 via a drive 46. During a forward motion (see arrow 45), the piston 41 can supply fluid in the piston cylinder 43 into the second irrigation fluid line 22. The valve 25 releases the volume flow in the direction toward the first irrigation fluid line 4, or interrupts the volume flow.

Figure 4:
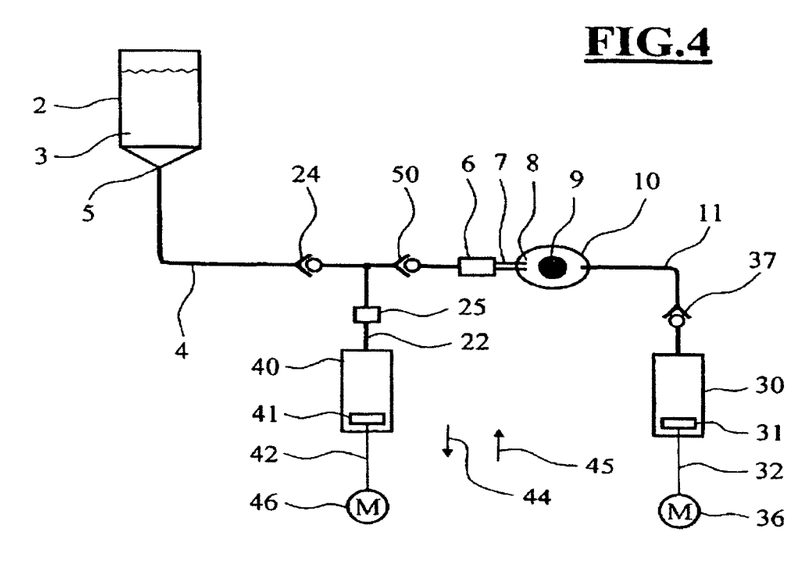
FIG. 4 shows a schematic illustration of a fourth embodiment of the ophthalmosurgical system according to the disclosure.

If a valve 50 is provided in the first irrigation fluid line 4 (see FIG. 4), this valve can be connected such that, during a backward motion (see arrow 44) of the piston 41, fluid flows from the first irrigation fluid source 2, through the first irrigation fluid line 4, the first valve 24, the second irrigation fluid line 22 and through the third valve 25. This allows the second irrigation fluid source 20 or 40 to be filled.

Figure 5:
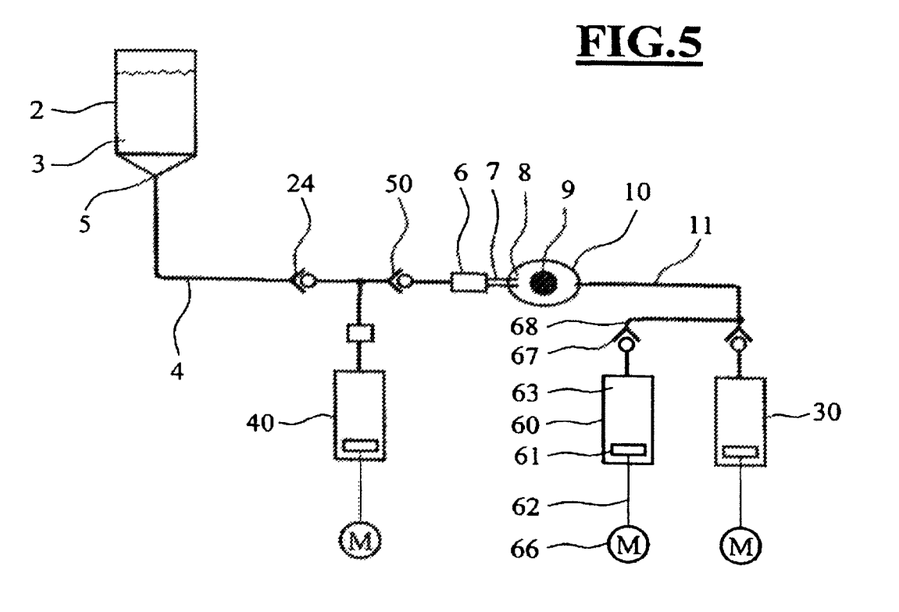
FIG. 5 shows a schematic illustration of a fifth embodiment of the ophthalmosurgical system according to the disclosure.

Negative pressure can form in the aspiration fluid line 11 if there is an occlusion or obstruction of the line 11 during aspiration. When the obstruction breaks open, this results in dangerous suction that can suction out too much fluid from the interior space of the eye. In order to prevent this (see FIG. 5), provision can be made for a third irrigation fluid source 60 with a piston 61, a piston rod 62 and a drive 66, which supplies irrigation fluid 63 via a fifth valve 67 to the aspiration fluid line 11 via a third irrigation fluid line 68 as a function of negative pressure in the aspiration fluid line 11. This can reliably prevent a collapse of the interior space of the eye.

Figure 6:
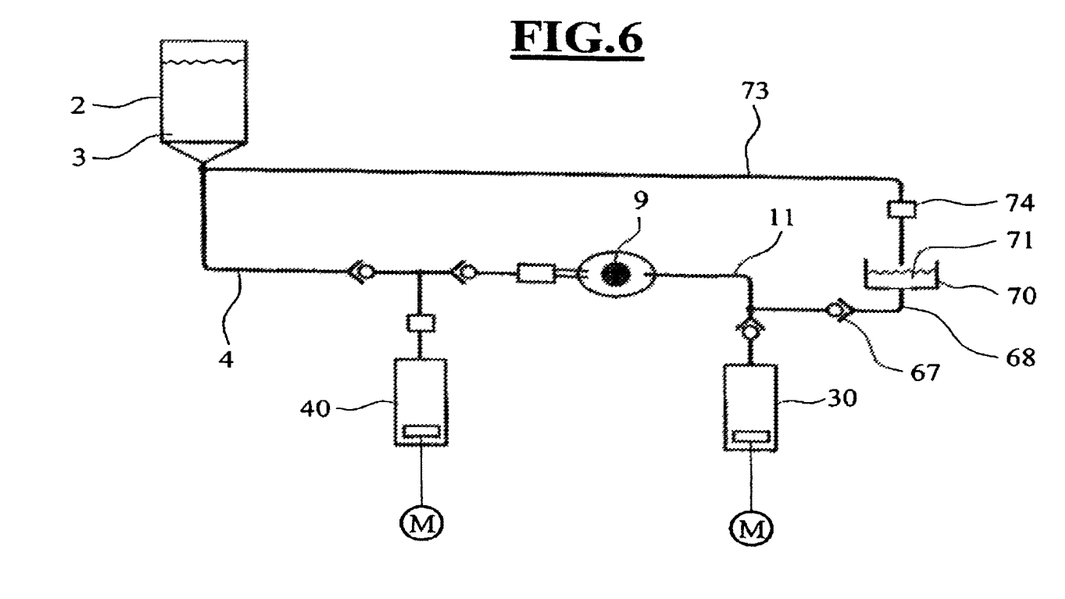
FIG. 6 shows a schematic illustration of a sixth embodiment of the ophthalmosurgical system according to the disclosure.

FIG. 6 shows that the third irrigation fluid source can be designed as a container 70 in a further embodiment of the disclosure, which container can supply the irrigation fluid 71 contained therein to the aspiration fluid line 11 via the third irrigation fluid line 68. In this embodiment, the third irrigation fluid source 70 is connected to the first irrigation fluid source 2 via a filling line 73 and a sixth valve 74. This reliably prevents pressure variation in the first irrigation line 4 when an occlusion is pierced in the aspiration fluid line 11.

What is claimed is:

1. A system, comprising:
   a first irrigation fluid source;
   a first irrigation fluid line connected to the first irrigation fluid source at a first end of the first irrigation fluid line, the first irrigation fluid line having a second end opposite the first end, the second end of the first irrigation fluid line being open so that a first irrigation fluid can be transported from the first irrigation fluid source and out of the second end of the first irrigation line;
   an aspiration fluid line configured to be in fluid communication with the second end of the first irrigation fluid line;
   a suction pump to which the aspiration fluid line is connected;
   a second irrigation fluid source to which a second irrigation fluid line is connected, the second irrigation fluid line being connected to the first irrigation fluid line at a coupling site so that both the first and second irrigation fluid sources are simultaneously in fluid communication with the first irrigation fluid line so that a second irrigation fluid can be supplied into the first irrigation fluid line from the second irrigation fluid line at the same time as the first irrigation fluid can be supplied into the first irrigation fluid line from the first irrigation fluid source, a fluid pressure from the first irrigation fluid source being capable of being built up using the second irrigation fluid source, the fluid pressure being higher than can be achieved with the first irrigation fluid source alone;
   a first valve between the first end of the first irrigation fluid line and the coupling site; and
   a second valve between the second irrigation fluid source and the coupling site,
   wherein the system is an ophthalmosurgical system.

2. The system of claim 1, wherein the suction pump comprises a piston pump, the piston pump comprises a controllable drive and a cylinder, and the piston pump is configured to hold an aspirated fluid in the cylinder.

3. The system of claim 1, further comprising a third valve, wherein the third valve is in the aspiration fluid line.

4. The system of claim 1, wherein the second irrigation fluid source comprises a piston pump, the piston pump comprises a controllable drive and a piston, and the piston pump is configured to dispense the second irrigation fluid contained in the piston into the second irrigation fluid line.

5. The system of claim 1, further comprising a third valve, wherein the third valve is in the first irrigation fluid line between the coupling site and the second end of the first irrigation fluid line.

6. The system of claim 1, further comprising:
   a third irrigation fluid line;
   a third irrigation fluid source connected to the aspiration fluid line via the third irrigation fluid line; and
   a third valve, the third valve being in the third irrigation fluid line.

7. The system of claim 6, wherein the third irrigation fluid source comprises a piston pump, the piston pump comprises a controllable drive and the piston, and the piston pump is configured to dispense a third irrigation fluid contained in the piston into the aspiration fluid line via the third irrigation fluid.

8. The system of claim 7, further comprising:
a filling line that connects the third irrigation fluid source to the first irrigation fluid source; and
a fourth valve, the fourth valve being in the filling line.

9. The system of claim 6, further comprising:
a filling line that connects the third irrigation fluid source to the first irrigation fluid source; and
a fourth valve, the fourth valve being in the filling line.

10. The system of claim 1, further comprising a third valve, wherein the third valve is in the aspiration fluid line, the suction pump comprises a first piston pump, the first piston pump comprises a controllable drive and a cylinder, and the first piston pump is configured to hold an aspirated fluid in the cylinder.

11. The system of claim 10, wherein the second irrigation fluid source comprises a second piston pump, the second piston pump comprises a controllable drive and a piston, and the second piston pump is configured to dispense the second irrigation fluid contained in the piston into the second irrigation fluid line.

12. The system of claim 11, further comprising a fourth valve, wherein the fourth valve is in the first irrigation fluid line between the coupling site and the second end of the first irrigation fluid line.

13. The system of claim 12, further comprising:
a third irrigation fluid line;
a third irrigation fluid source connected to the aspiration fluid line via the third irrigation fluid line; and
a fifth valve, the fifth valve being in the third irrigation fluid line.

14. The system of claim 1, further comprising a third valve, wherein the third valve is in the aspiration fluid line, the second irrigation fluid source comprises a piston pump, the piston pump comprises a controllable drive and a piston, and the piston pump is configured to dispense the second irrigation fluid contained in the piston into the second irrigation fluid line.

15. The system of claim 14, further comprising a fourth valve, wherein the fourth valve is in the first irrigation fluid line between the coupling site and the second end of the first irrigation fluid line.

16. The system of claim 15, further comprising:
a third irrigation fluid line;
a third irrigation fluid source connected to the aspiration fluid line via the third irrigation fluid line; and
a fifth valve, the fifth valve being in the third irrigation fluid line.

17. The system of claim 1, further comprising a third valve, wherein the third valve is in the first irrigation fluid line between the coupling site and the second end of the first irrigation fluid line, the second irrigation fluid source comprises a piston pump, the piston pump comprises a controllable drive in the piston, and the piston pump is configured to dispense the second irrigation fluid contained in the piston into the second irrigation fluid line.

18. The system of claim 17, further comprising:
a third irrigation fluid line;
a third irrigation fluid source connected to the aspiration fluid line via the third irrigation fluid line; and
a fourth valve, the fourth valve being in the third irrigation fluid line.

19. The system of claim 1, wherein the system is configured so that, during use, the first and second irrigation fluids are provided to an ocular lens via the second end in the first irrigation fluid line, and a fluid is removed from the ocular lens via the aspiration fluid line.

20. The system of claim 1, wherein:
the second valve has a first position and a second position;
when the second valve is in the first position, the first irrigation fluid line is in fluid communication with the second irrigation fluid line; and
when the second valve is in the second position, the first irrigation fluid line is not in fluid communication with the second irrigation fluid line.

21. The system of claim 1, wherein:
the second valve has a first position and a second position;
when the second valve is in the first position, the second irrigation fluid can be supplied into the first irrigation fluid line from the second irrigation fluid line; and
when the second valve is in the second position, the second irrigation fluid cannot be supplied into the first irrigation fluid line from the second irrigation fluid line.

* * * * *